United States Patent [19]

Goto et al.

[11] Patent Number: 4,946,497
[45] Date of Patent: * Aug. 7, 1990

[54] PYRIDINE-3-CARBOXAMIDES HAVING PLANT GROWTH REGULATING PROPERTIES

[75] Inventors: Yukihisa Goto; Kazuhisa Masamoto; Hiroshi Yagihara; Yasuo Morishima; Hirokazu Osabe, all of Himeji, Japan

[73] Assignee: Daicel Chemical Industries Ltd., Osaka, Japan

[*] Notice: The portion of the term of this patent subsequent to Jul. 4, 2006 has been disclaimed.

[21] Appl. No.: 274,616

[22] Filed: Nov. 22, 1988

Related U.S. Application Data

[63] Continuation of Ser. No. 945,396, Dec. 23, 1986, abandoned.

[30] Foreign Application Priority Data

Dec. 27, 1985 [JP] Japan ................. 60-2989153
Dec. 27, 1985 [JP] Japan ................. 60-2989154
Apr. 23, 1986 [JP] Japan ................. 61-94034
Apr. 23, 1986 [JP] Japan ................. 61-94035

[51] Int. Cl.$^5$ ................. C07D 211/84; C07D 211/86; C07D 211/90; A01N 43/40
[52] U.S. Cl. ................. 71/94; 546/291; 546/298; 546/300
[58] Field of Search ................. 546/291, 298, 300; 71/94

[56] References Cited

FOREIGN PATENT DOCUMENTS

| 115278 | 12/1981 | Canada ................. 546/298 |
| 40082 | 11/1981 | European Pat. Off. ................. 546/298 |
| 51-43783 | 4/1976 | Japan ................. 546/298 |
| 51-48686 | 4/1976 | Japan ................. 546/298 |
| 52-144676 | 5/1977 | Japan ................. 546/298 |
| 54-24892 | 2/1979 | Japan ................. 546/298 |

OTHER PUBLICATIONS

Zankowska 23(11), 901 (1975).
Zankowska 21, 141 (1976).
Yakugakuzassi (Yakugaku Zasshi), "Studies on Ketene and Its Derivatives", Kato et al., pp. 40–46 (1981).
Journal of Medicinal Chemistry, "Preparation and Anti-Inflammatory Activity of 2-and 4-Pyridones", Pierce et al., vol. 25, pp. 131–136 (1982).
Chemical Abstracts, vol. 88, 22565g, (1978).
Chemical Abstracts, vol. 85, 21037n (1976).

Primary Examiner—Alan L. Rotman
Attorney, Agent, or Firm—Bryan, Cave, McPheeters & McRoberts

[57] ABSTRACT

A compound of the formula (I)

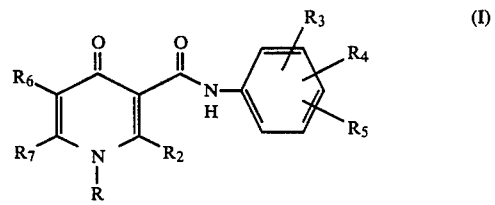

or a salt thereof, wherein R is hydrogen atom, or a group of —$(CH_2)_n$—$R_1$ wherein n is an integer from 1 to 3 and $R_1$ is hydrogen atom, hydroxy group, a lower alkoxy group, mercapto group, a lower alkylthio group, amino group, a di-lower alkylamino group, a $C_{3-11}$ alkyl group, a lower alkenyl group, a lower alkynyl group, a cycloalkyl group, a 5- or 6-membered heterocyclic group, or a phenyl group which may be substituted by one or two substituents of a halogen, a lower alkyl or a lower alkoxy;

$R_2$ and $R_7$ are the same, a $C_{1-11}$ alkyl group, a lower alkenyl group, a lower alkynyl group, a cycloalkyl group, a lower alkoxyalkyl group, an aralkyl group whose nucleus may be substituted by one or two substituents of a halogen, a lower alkyl or a lower alkoxy, or a halalkyl group;

$R_3$, $R_4$ and $R_5$ are, the same or different, hydrogen atom, a halogen atom, cyano group, nitro group, amino group, a lower alkyl group, a lower haloalkyl group, hydroxy group, a lower alkoxy group, an aryloxy group, carboxy group or a lower alkoxycarbonyl group;

$R_6$ is hydrogen atom, a halogen atom, a lower alkyl group, a phenyl group which may be substituted or an aralkyl group which may be substituted; and in the case of $R_2$ and $R_7$ being methyl group, $R_6$ is a lower alkyl group, a phenyl group which may be substituted or an aralkyl group which may be substituted, which is useful as a plant growth inhibitor.

11 Claims, No Drawings

PYRIDINE-3-CARBOXAMIDES HAVING PLANT GROWTH REGULATING PROPERTIES

This is a continuation of U.S. Ser. No. 945,396, filed 12/23/86.

BACKGROUND OF THE INVENTION

1. Field of the Invention

This invention relates to novel compounds which belong to 1,4-dihydro-4-oxo-3-pyridinecarboxamides. The compounds of this invention show growth inhibitory activities on plants and also antiinflammatory activity.

2. Description of the Prior Arts

Some compounds belonging to 1,4-dihydro-4-oxo-3-pyridinecarboxamides are found in literatures.

In Bull. Acad. Pol. Sci., Ser. Sci. Chim. 23(11), 901 (1975), Zankowska-Jasinska. W. et al., reported on N-(4-chlorophenyl)-1,4-dihydro-4-oxo-1,2,6-triphenyl-3-pyridinecarboxamide and 1-(4-chlorophenyl)-1,4-dihydro-4-oxo-N,2,6-triphenyl-3-pyridinecarboxamide. In Zesz. Nauk. Uniw. Jagiellon., Pr. Chim, 21., 141 (1976), Zankowska-Jasinska. W. et al., reported on 1,4-dihydro-4-oxo-N,2,6-triphenyl-3-pyridinecarboxamide, 1,4-dihydro-4-oxo-N,1,2,6-tetraphenyl-3-pyridinecarboxamide, 1,4-dihydro-2,6-dimethyl-4-oxo-N,1-diphenyl-3-pyridinecarboxamide.

In Yakugakuzassi, 101, 40 (1981), Kato et al. reported on four compounds, namely N-(4-chlorophenyl)-1,4-dihydro-2,6-dimethyl-4-oxo-3-pyridinecarboxamide, 1,4-dihydro-2,6-dimethyl-4-oxo-N-phenyl-1-(phenylmethyl)-3-pyridinecarboxamide, 1,4-dihydro-N-(4-methoxyphenyl)-2,6-dimethyl-4-oxo-1-(phenylmethyl)-3-pyridinecarboxamide and N-(4-chlorophenyl)-1,4-dihydro-2,6-dimethyl-4-oxo-1-(phenylmethyl)-3-pyridinecarboxamide, as one of the studies on reactivity of ketene derivatives but they did not refer to utility thereof. Canadian Patent No. 1,115,278 [and also J. B. Pierce et al, J. Med. Chem. 25, 131 (1982)], there are disclosed 4-pyridone compounds possessing antiinflammatory activity, i.e., 1,4-dihydro-2,6-dimethyl-4-oxo-N,1-diphenyl-3-pyridinecarboxamide, N,1-dibutyl-1,4-dihydro-2,6-dimethyl-4-oxo-3-pyridinecarboxamide, N,1-didodecyl-1,4-dihydro-2,6-dimethyl-4-oxo-3-pyridinecarboxamide, N-(4-chlorophenyl)-1-ethyl-1,4-dihydro-2,6-dimethyl-4-oxo-3-pyridinecarboxamide, etc.

Cephalosporins which contain a partial structure of 1,4-dihydro-4-oxo-3-pyridinecarboxamide are known as medicine in Japanese Patent Unexamined Publication Nos. Sho 54(1979)-24892, Sho 51(1976)-43783 and Sho 51(1976)-48686.

On the other hand, 1,4-dihydro-4-oxo-3-pyridinecarboxylic acid derivatives as compounds which show plant growth regulating activity, especially chemical hybridizing activity, are known in Japanese Patent Unexamined Publication Nos. Sho 52(1977)-144676 (see also U.S. Pat. No. 4,051,142) and Sho 57(1982)-114573 (see also E.P. No. 40,082). However, plant growth inhibitory agents whose active ingredients are 1,4-dihydro-4-oxo-3-pyridinecarboxamide as in the formula (I) shown below are not known.

SUMMARY OF THE INVENTION

This invention provides a compound of the formula (I)

or a salt thereof, wherein R is hydrogen atom or a group of —(CH$_2$)$_n$—R$_1$ in which n is an integer from 1 to 3 and R$_1$ is hydrogen atom, hydroxy group, a lower alkoxy group, mercapto group, a lower alkylthio group, amino group, a di-lower alkylamino group, a C$_{3-11}$ alkyl group, a lower alkenyl group, a lower alkynyl group, a cycloalkyl group, a 5- or 6-membered heterocyclic group, or a phenyl group which may be substituted by one or two substituents of halogen, lower alkyl or lower alkoxy;

R$_2$ and R$_7$ are the same and are C$_{1-11}$ alkyl group, a lower alkenyl group, a lower alkynyl group, a cycloalkyl group, a lower alkoxyalkyl group, an aralkyl group whose nucleus may be substituted by one or two substituents of a halogen, a lower alkyl or a lower alkoxy, or a haloalkyl group; R$_3$, R$_4$ and R$_5$ are, the same or different, hydrogen atom, a halogen atom, cyano group, nitro group, amino group, a lower alkyl group, a lower haloalkyl group, hydroxy group, a lower alkoxy group, an aryloxy group, carboxy group or a lower alkoxycarbonyl group;

R$_6$ is hydrogen atom, a halogen atom, a lower alkyl group, a phenyl group which may be substituted or an aralkyl group which may be substituted; and in the case of R$_2$ and R$_7$ being methyl group, R$_6$ is a lower alkyl group, a phenyl group which may be substituted or an aralkyl group which may be substituted.

This invention also provides plant growth inhibitors which contain at least one kind of compounds of the formula (I) and salts thereof as active ingredient.

DESCRIPTION OF PREFERRED EMBODIMENTS

The term of "lower" used for the lower alkyl, lower alkoxy or like group in this invention means a group containing 1-5 carbon atoms. Specifically, the lower alkyl group may be methyl, ethyl, propyl, isopropyl, butyl, isobutyl, pentyl or isopentyl; the lower alkoxy group may be methoxy, ethoxy, propoxy, isopropoxy or butoxy; the lower alkoxycarbonyl group may be methoxycarbonyl, ethoxycarbonyl, propoxycarbonyl or butoxycarbonyl; or the lower alkylthio group may be methylthio, ethylthio, propylthio, isopropylthio, butylthio or pentylthio. The lower alkenyl or lower alkynyl group may be vinyl, allyl, isopropenyl 2-butenyl, 1,3-butadienyl, 2-pentenyl 1,4-pentadienyl, 1,6-heptadienyl, 1-hexenyl, ethynyl or 2-propynyl.

Examples of the cycloalkyl group include cyclopropyl, cyclopentyl and cyclohexyl.

Examples of the lower haloalkyl group include trifluoromethyl, chloromethyl and the like.

Examples of the lower alkoxyalkyl group include methoxymethyl, ethoxymethyl, propoxymethyl, butoxymethyl and the like.

Examples of the lower alkylthioalkyl group include methylthiomethyl, ethylthiomethyl, methylthioethyl, ethylthioethyl and the like.

The halogen atom includes chlorine, bromine, fluorine and iodine.

Examples of the aralkyl group include benzyl, 3-phenyl-propyl, 4-phenylbutyl and the like.

Examples of the aryloxy group include phenyloxy, naphthyloxy and the like.

The 5- or 6-membered heterocyclic group includes 5- or 6-membered one containing one to three hetero atoms selected from nitrogen atom, oxygen atom and sulfur atom. Examples of the 5-membered heterocyclic group are furyl, tetrahydrofuryl, thienyl, thiazolyl, isothiazolyl, oxazolyl, isooxazolyl or pyrazolyl and the 6-membered heterocyclic group are pyridyl, pyrimidinyl, pyrazinyl or pyridazinyl. These heterocyclic groups may be substituted by an alkyl as methyl or ethyl, a halogen atom or phenyl. When the heterocyclic group is substituted by phenyl, it may form a condensed ring combining the two adjacent carbon atoms in the heterocyclic group with phenyl group. Examples of the condensed ring are benzothiazolyl, benzofuryl, quinazolinyl or quinoxalinyl group.

Examples of the substituent of the phenyl group and the aralkyl group which may be substituted include halogen atom, lower alkyl, lower alkoxy, trihaloalkyl, nitro, cyano and the like, and the number of the substituents is preferably one or two.

The compound of the formula (I) in this invention may form an addition salt with an acid such as hydrochloric acid, sulfuric acid, phosphoric acid, methanesulfonic acid, p-toluenesulfonic acid or trifluoroacetic acid when sufficiently basic, and also form a salt with an inorganic base when it contains a carboxylic group. Such salts are also included in this invention.

The compound of the formula (I) in this invention may be prepared by any of the following methods.

METHOD A (Method A)

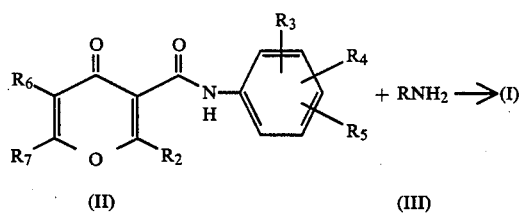

(II)             (III)

[R, $R_2$, $R_3$, $R_4$, $R_5$, $R_6$ and $R_7$ of the formula (II) and (III) are the same as those in the formula (I)].

This method comprises reacting a 4-pyrone derivative (II), that is 4-oxo-N-phenyl-4H-pyran-3-pyridinecarboxamide, with ammonia or an amine (III) or their salt in an appropriate solvent (e.g., ethanol, water, toluene, ethyl ether, methylene chloride, chloroform or the like) at a temperature of e.g., room temperature to 60° C. One or more moles of ammonia or the amine is used, per one mole of the 4-pyrone derivative. To accelerate this reaction, a base, such as sodium carbonate or sodium hydroxide may be added to the reaction mixture.

METHOD B (Method B)

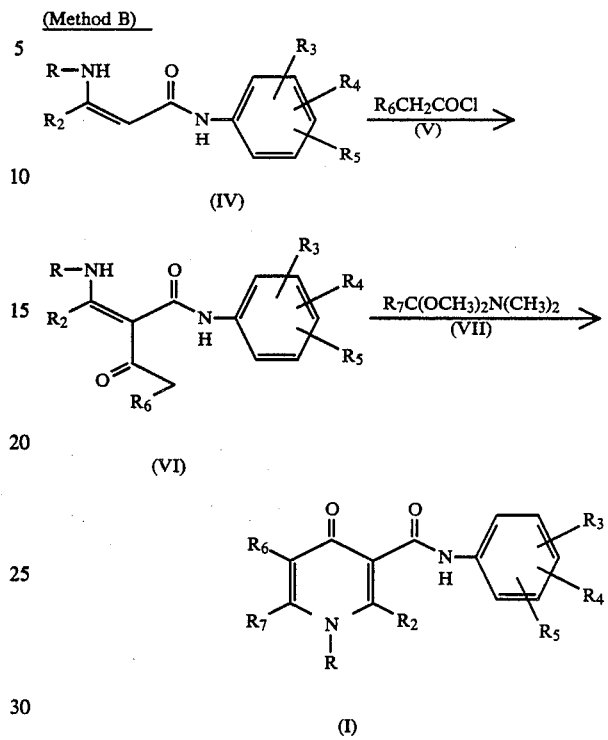

[R, $R_2$, $R_3$, $R_4$, $R_5$, $R_6$ and $R_7$ in the formula (IV), (V), (VI) and (VII) are the same as those in the formula (I)].

This method comprises reacting an 3-aminocrotonic acid anilide derivative (IV) with an acid halide (V) in the presence of a base to yield a compound of the formula (VI), and then reacting this compound (VI) with a N,N-dimethylamide dimethylketal derivative (VII). Preferred examples of the base include pyridine, picoline or triethylamine. The reaction between the aminocrotonic acid anilide derivative (IV) and the acid halide (V) is usually conducted in an inert solvent such as a halogenated hydrocarbon (e.g., methylene chloride) at a temperature of room temperature to ice-cooled one. The reaction between the compound (VI) and the ketal derivative (VII) is preferably conducted under reflux of an inert solvent used (e.g., benzene) and in the presence of the above mentioned base. This method is useful to synthesize a compound of the formula (I) in which $R_6$ is aryl group.

For application as a plant growth inhibitor (e.g., herbicide or plant growth retardant), the compound of the present invention (I) is generally formulated into compositions. These compositions can be solids such as dusts, granules, or wettable powders; or they can be liquids such as solutions, aerosols, or emulsifiable concentrates.

For example, solid compositions such as dusts, wettable powders or granules can be prepared by blending the active compound with a solid inert carrier such as the kaolinites, bentonites, clays, talcs, silicas and the like. Liquid compositions such as solutions or emulsifiable concentrates can be prepared by dissolving the active compound with a liquid inert solvent such as xylene, methylnaphthalein, ethanol, isopropanol, ethylene glycol, methyl cellosolve, acetone, isophorone, cyclohexanone, soybean oil, cotton-seed oil, dimethyl formamide, dimethyl sulfoxide, acetonitrile, water and so on.

Surface active agents for wetting, dispersing or emulsifying are generally used with the compositions as above defined. For example; polyoxyethylene-alkyl ethers, polyoxyethylene-sorbitan fatty acid esters, and other nonionic types; alkyl and alkaryl sulfonates and sulfates and their sodium salts and other anionic types or other types of surface active agents.

For pre-emergence applications these compositions are usually applied either as sprays, dusts, or granules in the area in which suppression of vegetation is desired. For post-emergence applications control of established plant growth, sprays or dusts are most commonly used. These formulations may contain 10–80% for wettable powders, 1–10% for granules, or 10–50% for emulsifiable concentrates by weight of active ingredient. Dosage of these compositions is generally 0.1–2 Kg by weight of the active ingredient.

This invention is illustrated further by examples hereinafter. Also, growth-inhibitory activities on plants of the compounds of the invention are shown in reference examples.

Furthermore, related specific compounds in addition to the compounds shown in the examples are as follows;

2,6-diethyl-1,4-dihydro-4-oxo-N-phenyl-1-(2-pyridylmethyl)-3-pyridine-carboxamide,
2,6-diethyl-1,4-dihydro-4-oxo-N-phenyl-1-(3-pyridylmethyl)-3-pyridine-carboxamide,
2,6-diethyl-1,4-dihydro-4-oxo-N-phenyl-1-(4-pyridylmethyl)-3-pyridine-carboxamide,
2,6-diethyl-1-(2-furylmethyl)-1,4-dihydro-4-oxo-N-phenyl-3-pyridine-carboxamide,
1-cyclohexylmethyl-2,6-diethyl-1,4-dihydro-4-oxo-N-phenyl-3-pyridine-carboxamide,
2,6-diethyl-1,4-dihydro-N-(2-methylphenyl)-4-oxo-1-phenylmethyl-3-pyridine-carboxamide,
N-(2-chlorophenyl)-2,6-diethyl-1,4-dihydro-4-oxo-1-phenylmethyl-3-pyridine-carboxamide,
2,6-diethyl-N-(2-ethylphenyl)-1,4-dihydro-4-oxo-1-(3-phenylpropyl)-3-pyridinecarboxamide,
2,6-diethyl-1,4-dihydro-N-(2,3-dimethylphenyl)-4-oxo-1-(2-phenylethyl)-3-pyridinecarboxamide,
2,6-diethyl-1-hexyl-1,4-dihydro-N-(2,6-dimethylphenyl)-4-oxo-3-pyridine-carboxamide.
1-butyl-2,6-diethyl-N-(2,6-diethylphenyl)-1,4-dihydro-4-oxo-3-pyridine-carboxamide,
2,6-diethyl-N-(2-ethyl-6-methylphenyl)-1,4-dihydro-4oxo-1-pentyl-3-pyridinecarboxamide,
1,4-dihydro-4-oxo-N-phenyl-2,6-dipropyl-1-(3-pyridylmethyl)-3-pyridine-carboxamide,
1,4-dihydro-4-oxo-N-phenyl-2,6-dipropyl-1-(4-pyridylmethyl)-3-pyridine-carboxamide,
1-(2-furylmethyl)-1,4-dihydro-4oxo-N-phenyl-2,6-dipropyl-3pyridine-carboxamide,
1,4-dihydro-N-(2-methylphenyl)-4-oxo-1-phenylmethyl-2,6-dipropyl-3-pyridine-carboxamide,
1-(4-chlorophenylmethyl)-1,4-dihydro-N-(2-methylphenyl)-4-oxo-2,6-dipropyl-3-pyridinecarboxamide,
5-bromo-1-butyl-2,6-diethyl-N-(2,6-diethylphenyl)-1,4-dihydro-4oxo-3-pyridinecarboxamide,
2,6-diethyl-N-(2,6-diethylphenyl)-1,4-dihydro-5-methyl-4-oxo-1-(2phenyl-ethyl)-3pyridinecarboxamide,
2,6-dibutyl-1,4-dihydro-4-oxo-N-phenyl-1-phenylmethyl-3pyridinecarboxamide,
2,6-dibutyl-1,4-dihydro-1-(4-methylphenylmethyl)-4-oxo-N-phenyl-3-pyridinecarboxamide,
2,6-dibutyl-1-(4-chlorophenylmethyl)-1,4-dihydro-N-(2-methylphenyl)-4-oxo-3-pyridinecarboxamide,
1,4-dihydro-4-oxo--2,6-dipentyl-N-phenyl-1-phenylmethyl-3-pyridine-carboxamide,
1,4-dihydro-2,5,6-trimethyl-4-oxo-N-phenyl-1-(2-pyridylmethyl)-3-pyridine-carboxamide,
1,4-dihydro-2,5,6-trimethyl-1-(4-methylphenylmethyl)-4-oxo-N-phenyl-3-pyridinecarboxamide,
1,4-dihydro-2,5,6-trimethyl-4-oxo-N-phenyl-1(4pyridylmethyl)-3-pyridinecarboxamide,
1-(2-furylmethyl)-1,4-dihydro-2,5,6-trimethyl-4-oxo-N-phenyl-3-pyridine-carboxamide,
1,4-dihydro-2,5,6-trimethyl-N-(2-methylphenyl)-4oxo-1-phenylmethyl-3-pyridinecarboxamide,
1-(4-chlorophenylmethyl)-1,4-dihydro-2,5,6-trimethyl-N-(2-methylphenyl)-4-oxo-3-pyridinecarboxamide,
N-(2-chlorophenyl)-1,4-dihydro-2,5,6-trimethyl-4-oxo-1-phenylmethyl-3-pyridinecarboxamide,
1-butyl-1,4-dihydro-2,5,6-trimethyl-N-(2,6-dimethylphenyl)-4-oxo-3-pyridine-carboxamide,
N-(2,6-diethylphenyl)-1,4-dihydro-1-isobutyl-2,5,6-trimethyl-4-oxo-3-pyridinecarboxamide,
N-(2,6-diethylphenyl)-1,4-dihydro-2,5,6-trimethyl-4-oxo-1-pentyl-3-pyridine-carboxamide,
N-(2,6-diethylphenyl)-1,4-dihydro-1-isopentyl-2,5,6-trimethyl-4-oxo-3-pyridinecarboxamide,
N-(2,6-diethylphenyl)-1-hexyl-1,4-dihydro-2,5,6-trimethyl-4-oxo-3-pyridine-carboxamide,
N-(2,6-diethylphenyl)-1,4-dihydro-2,5,6-trimethyl-4-oxo-1-(3-phenylpropyl)-3-pyridinecarboxamide,
1-butyl-N-(2-ethyl-6-methylphenyl)-1,4-dihydro-2,5,6-trimethyl-4-oxo-3-pyridinecarboxamide,
N-(2-ethyl-6-methylphenyl)-1,4-dihydro-2,5,6-trimethyl-4-oxo-1-(2-phenyl-ethyl)3-pyridinecarboxamide,
N-(2,3-dichlorophenyl)-1,4-dihydro-1-isobutyl-2,5,6-trimethyl-4-oxo-3-pyridinecarboxamide,
N-(2,4-dichlorophenyl)-1,4-dihydro-2,5,6-trimethyl-4-oxo-1-pentyl-3-pyridinecarboxamide,
N-(2,5-dichlorophenyl)-1,4-dihydro-1-isopentyl-2,5,6-trimethyl-4-oxo-3-pyridinecarboxamide,
N-(2,6-dichlorophenyl)-1-hexyl-1,4-dihydro-2,5,6-trimethyl-4-oxo-3-pyridinecarboxamide,
N-(4-bromo-2,6-diethylphenyl)-1-butyl-1,4-dihydro-2,5,6-trimethyl-4oxo-3-pyridinecarboxamide,
N-(4-bromo-2,6-diethylphenyl)-1,4-dihydro-2,5,6-trimethyl-4-oxo-1(2phenylethyl)-3-pyridinecarboxamide,
N-(4-bromo-2,6-diethylphenyl)-1,4-dihydro-2,5,6-trimethyl-4-oxo-1-propyl-3-pyridinecarboxamide,
N-(4-bromo-2,6-diethylphenyl)-1,4-dihydro-2,5,6-trimethyl-4-oxo-1-pentyl-3-pyridinecarboxamide,
1-butyl-N-(4-chloro-2,6-diethylphenyl)-1,4-dihydro-2,5,6-trimethyl-4-oxo-3-pyridinecarboxamide,
N-(4-chloro-2,6-diethylphenyl)-1,4-dihydro-2,5,6-trimethyl-4-oxo-1-propyl-3-pyridinecarboxamide, and
N-(4-chloro-2,6-diethylphenyl)-1,4-dihydro-2,5,6-trimethyl-4-oxo-1-pentyl-3pyridinecarboxamide.

PRODUCTION EXAMPLE

1,4-Dihydro-2,5,6-trimethyl-4-oxo-N-phenyl-1-(2-phenylethyl) -3-pyridinecarboxamide (Example No. 15)

To a mixture of 1 g (3.89 mmol) of 2,5,6-trimethyl-4-oxo-N-phenyl-4H-pyran-3-carboxamide, 0.71 g (5.83 mmol) of β-phenethylamine and 5 ml of toluene, 0.4 ml of 1N solution of sodium hydroxide in methanol were added and stirred overnight at room temperature. After addition of about 10 ml of water and about 10 ml of ether, the mixture was shaken and allowed to stand. The crystals precipitated were separated by filtration and dried in vacuo to afford 1.16 g of the title compound having m.p. 191°-193° C.

PRODUCTION EXAMPLE

1-Butyl-N-(2,6-diethylphenyl)-1,4-dihydro-2,6-dimethyl -4-oxo-5-phenyl-3-pyridinecarboxamide (Example No. 10)

A mixture of 11.67 g (50 mmol) of N-(2,6-diethylphenyl)-3-oxo-butanamide, 4.02 g (55 mmol) of butylamine and 100 ml of toluene was stirred at 50° C. for 1 hour, and then under refluxing for 1 hour after adding three drops of acetic acid, while the resulted water and excess of butylamine were distilled off together with about 24 ml of toluene. 4.35 g (55 mmol) of pyridine and 120 ml of methylene chloride were added to the residue obtained by concentration of the reaction mixture in vacuo, to make it in homogeneous solution. While ice cooling, a mixture of 0.61 ml (50 mmol) of phenyl acetyl chloride and 20 ml of methylene chloride was dropwise added to the solution within 30 mins., and stirred for an hour.

The reaction mixture was mixed with cold water and transferred into a separatory funnel to separate an aqueous layer and an organic layer. The organic layer was dried and concentrated in usual manner and the residue was crystallized from isoprpyl ether to afford 15.17 g of 3-butylamino-N-(2,6-diethylphenyl)-2-phenylacetyl-2-butenic acid amide.

A mixture of 4.07 g (10 mmol) of the resulted 3-butylamino-N-(2,6-diethylphenyl)-2-phenylacetyl-2-butenic acid amide, 4.00 g (30 mmol) of N,N-dimethylacetamide dimethyl ketal, 0.4 ml of trimethylamine and 20 ml of benzene was refluxed for 3 hours under nitrogen atmosphere. The residue, obtained by concentrating the reaction mixture under vacuo, was column-chromatographed on silica gel to afford 1.87 g of the title compound, as oil.

PRODUCTION EXAMPLE

1-Butyl-1,4-dihydro-4-oxo-N-phenyl-2,6-dipropyl-3-pyridinecarboxamide (Example No. 3)

To a mixture of 1 g (3.34 mmol) of 4-oxo-N-phenyl-2,6-dipropyl-4H-pyran-3-carboxamide, 0.37 g (5.01 mmol) of butylamine and 5 ml of toluene, 1 ml of 1N sodium hydroxide solution in methanol was added and stirred overnight at room temperature. After adding about 10 ml of water and about 10 ml of ethylacetate to the mixture, they were well shaken in a separatory funnel. The organic layer was washed with saturated sodium chloride solution, dried in an usual manner, concentrated and crystallized from toluene and cyclohexane to afford 737 mg of the title compound having m.p. 133.5°-136.5° C.

The following Table 1 and Table 2 show physical properties of the compounds associated with this invention. Numbers in the column "Evaluation" in Table 2 were obtained as follows.

A carrier was prepared by mixing 50 parts (by weight) of talc, 25 parts of bentonite, 2 parts of Solpole-9047 (Toho Chemical Co., Ltd., Japan) and 3 parts of Solpole-5039 (Toho Chemical Co., Ltd., Japan). 50 parts of the test compound and 200 parts of the carrier were mixed to obtain 20% wettable powder, followed by dispersing the powder in distilled water to make a dispersion of the definite concentrations.

Seeds of *Oryza sativa L.*, *Echinochloa crus-galli L.*, and *Raphanus sativus L.* were germinated in a laboratory dish, to which the dispersion was added. After breeding for 7 days in a thermostatic box kept at 25° C. under illumination of fluorescent tubes, growth of plant was observed. In the column of "Evaluation" of Table 2, the designation 1 denotes no influence, 2 denotes 25% growth inhibition, 3 denotes 50% growth inhibition, 4 denotes 75% growth inhibition and 5 denotes 100% growth inhibition.

TABLE 1

| Example No. | R | $R_2, R_7$ | $R_3$ | $R_4$ | $R_5$ | $R_6$ | Melting point (°C.) | Molecular formula | Method |
|---|---|---|---|---|---|---|---|---|---|
| 1 | phenylmethyl | propyl | H | H | H | H | | $C_{25}H_{28}N_2O_2$ | A |
| 2 | " | ethyl | " | " | " | " | 110-111 | $C_{23}H_{24}N_2O_2$ | " |
| 3 | butyl | propyl | " | " | " | " | 133.5-136.5 | $C_{22}H_{30}N_2O_2$ | " |
| 4 | 4-methyl phenylmethyl | " | " | " | " | " | | $C_{26}H_{30}N_2O_2$ | " |
| 5 | cyclohexylmethyl | " | " | " | " | " | 99.5-100.5 | $C_{25}H_{34}N_2O_2$ | " |
| 6 | 2-pyridylmethyl | " | " | " | " | " | 93.5-95 | $C_{24}H_{27}N_3O_2$ | " |
| 7 | H | ethyl | 2-ethyl | 6-ethyl | " | " | | $C_{20}H_{26}N_2O_2$ | " |
| 8 | 4-methyl-phenylmethyl | " | H | H | " | " | 124-125 | $C_{24}H_{26}N_2O_2$ | |
| 9 | 4-chloro-phenylmethyl | propyl | 2-methyl | " | " | " | | $C_{26}H_{29}ClN_2O_2$ | " |
| 10 | butyl | $CH_3$ | 2-ethyl | 6-ethyl | H | phenyl | | $C_{28}H_{34}N_2O_2$ | B |
| 11 | phenylmethyl | " | " | " | " | methyl | 172-174 | $C_{26}H_{30}N_2O_2$ | A |
| 12 | butyl | " | " | " | " | " | 111-112 | $C_{28}H_{32}N_2O_2$ | " |
| 13 | 2-phenylethyl | " | " | " | " | " | 139-140 | $C_{27}H_{32}N_2O_2$ | " |
| 14 | phenylmethyl | " | H | H | " | " | 176-177.5 | $C_{22}H_{22}N_2O_2$ | " |
| 15 | 2-phenylethyl | $CH_3$ | H | H | H | methyl | 191-193 | $C_{28}H_{24}N_2O_2$ | A |
| 16 | butyl | " | 2-ethyl | 6-ethyl | " | ethyl | 117.5-120.5 | $C_{24}H_{34}N_2O_2$ | " |
| 17 | 2-phenylethyl | " | " | " | " | " | | $C_{28}H_{34}N_2O_2$ | |
| 18 | butyl | " | 2-methyl | 3-methyl | " | methyl | 258-262 | $C_{21}H_{28}N_2O_2$ | " |
| 19 | 2-phenylethyl | " | " | " | " | " | 201.5-204.5 | $C_{25}H_{28}N_2O_2$ | |
| 20 | butyl | " | 2-chloro | 6- | " | " | 166.5-169 | $C_{20}H_{25}ClN_2O_2$ | " |

TABLE 1-continued

| | | | | methyl | | | | | |
|---|---|---|---|---|---|---|---|---|---|
| 21 | 2-phenylethyl | " | " | " | " | " | 208.5–210.5 | $C_{24}H_{25}ClN_2O_2$ | " |
| 22 | butyl | " | 2-methyl | 3-chloro | " | " | 139.5–140.5 | $C_{20}H_{25}ClN_2O_2$ | " |
| 23 | 2-phenylethyl | " | " | " | " | " | 200–202 | $C_{24}H_{25}ClN_2O_2$ | " |
| 24 | " | " | 2-ethyl | H | " | " | 142.5–144.5 | $C_{25}H_{28}N_2O_2$ | " |
| 25 | butyl | " | " | 6-ethyl | " | " | | $C_{29}H_{36}N_2O_2$ | " |
| 26 | 2-phenylethyl | " | " | " | " | phenylmethyl | | $C_{33}H_{36}N_2O_2$ | " |
| 27 | H | " | " | " | " | methyl | 213–215 | $C_{19}H_{24}N_2O_2$ | " |
| 28 | butyl | " | " | " | 4-bromo | " | 144–146 | $C_{28}H_{31}BrN_2O_2$ | " |

TABLE 2

| Example No. | IR $\nu$ value (cm$^{-1}$) | Method | NMR Chemical shift δ value | Solvent | Conc. (ppm) | Evaluation Plants X | Y | Z |
|---|---|---|---|---|---|---|---|---|
| 1 | 1600, 1627, 1670 | Neat | 0.93(t, 3H), 1.00(t, 3H), 1.25–2.15(m, 4H), 2.47(t, 2H), 2.80–3.45(br, 2H), 5.16(s, 2H), 6.40(s, 1H), 6.60–7.80(m, 10H), 12.78(br, 1H) | CDCl$_3$ | 20<br>100 | 4<br>4 | 4<br>4 | 1<br>4 |
| 2 | 1600, 1628, 1670 | KBr | 1.21(t, 3H), 1.37(t, 3H), 2.54(q, 2H), 2.90–3.70(br, 2H), 5.23(s, 2H), 6.70–7.80(m, 10H), 12.80(br, 1H) | CDCl$_3$ | 20<br>100 | 4<br>4 | 4<br>4 | 1<br>2 |
| 3 | 1627, 1673 | KBr | 0.60–2.20(m, 17H), 2.57(t, 2H), 3.00–3.60(br, 2H), 3.90(t, 2H), 6.35(s, 1H), 6.70–7.80(m, 5H), 12.70(br, 1H) | CDCl$_3$ | 20<br>100 | 4<br>4 | 4<br>4 | 1<br>1 |
| 4 | 1625, 1665 | Neat | 0.93(t, 3H), 1.00(t, 3H), 1.25–2.15(m, 4H), 2.30(s, 3H), 2.47(t, 2H), 2.90–3.50(br, 2H), 5.15(s, 2H), 6.43(s, 1H), 6.55–7.80(m, 9H), 12.76(br, 1H) | CDCl$_3$ | 20<br>100 | 4<br>4 | 4<br>4 | 1<br>3 |
| 5 | 1625, 1667 | KBr | 0.60–2.10(m, 20H), 2.40–2.85 (m, 1H), 2.48(t, 2H), 3.07(t, 2H), 3.79(d, 2H), 6.33(s, 1H), 6.80–7.80(m, 5H), 12.60(br, 1H) | CDCl$_3$ | 20<br>100 | 4<br>4 | 4<br>4 | 1<br>1 |
| 6 | 1600, 1627, 1663 | KBr | 0.93(t, 3H), 1.01(t, 3H), 1.25–2.20(m, 4H), 2.48(t, 2H), 2.80–3.50(br, 2H), 5.28(s, 2H), 6.43(s, 1H), 6.50–8.60(m, 9H), 12.68(br, 1H) | CDCl$_3$ | 20<br>100 | 4<br>4 | 4<br>4 | 1<br>1 |
| 7 | 1653 | Neat | 1.14(t, 12H), 2.48(q, 2H), 2.60(q, 4H), 3.14(q, 2H), 6.24(s, 1H), 6.90–7.15(m, 3H), 11.25(br, 1H), 12.35(br, 1H) | CDCl$_3$ | 20<br>100 | 1<br>1 | 3<br>4 | 1<br>4 |
| 8 | 1600, 1623, 1667 | KBr | 1.21(t, 3H), 1.37(t, 3H), 2.30(s, 3H), 2.54(q, 2H), 2.90–3.55(br, 2H), 5.18(s, 2H), 6.45(s, 1H), 6.55–7.80(m, 9H), 12.83(br, 1H) | CDCl$_3$ | 20<br>100 | 4<br>4 | 4<br>4 | 1<br>1 |
| 9 | 1627, 1670 | Neat | 0.96(t, 3H), 1.01(t, 3H), 1.20–2.20(m, 4H), 2.41(s, 3H), 2.46(t, 2H), 2.70–3.55(br, 2H), 5.17(s, 2H), 6.44(s, 1H), 6.60–8.10(m, 8H), 12.53(br, 1H) | CDCl$_3$ | 20<br>100 | 4<br>4 | 4<br>4 | 1<br>1 |
| 10 | 1613, 1675 | Neat | 0.60–2.00(m, 7H), 1.13(t, 6H), 2.21(s, 3H), 2.63(q, 4H), 2.88(s, 3H), 3.98(t, 2H), 6.90–7.50(m, 8H), 11.60(br, 1H) | CDCl$_3$ | 20<br>100 | 1<br>3 | 2<br>2 | 4<br>4 |
| 11 | 1615, 1648 | KBr | 1.20(t, 6H), 2.20(s, 3H), 2.32(s, 3H), 2.68(q, 4H), 2.80(s, 3H), 5.26(s, 2H), 6.80–7.50(m, 8H), 11.73(br, 1H) | CDCl$_3$ | 20<br>100 | 1<br>1 | 1<br>2 | 4<br>4 |
| 12 | 1610, 1648 | KBr | 0.60–2.00(m, 7H), 1.17(t, 6H), 2.14(s, 3H), 2.40(s, 3H), 2.66(q, 4H), 2.84(s, 3H), 3.96(t, 2H), 7.03(s, 3H), 11.73(br, 1H) | CDCl$_3$ | 20<br>100 | 4<br>5 | 4<br>5 | 5<br>5 |
| 13 | 1620, 1650 | KBr | 1.17(t, 6H), 2.13(s, 3H), 2.39(s, 3H), 2.65(q, 4H) 2.87(s, 3H), 2.94(t, 2H), 4.17(t, 2H), 6.90–7.40(m, 8H), 11.65(br, 1H) | CDCl$_3$ | 20<br>100 | 5<br>5 | 5<br>5 | 5<br>5 |
| 14 | 1620, 1663 | KBr | 2.13(s, 3H), 2.23(s, 3H), 2.78(s, 3H), 5.16(s, 2H) 6.60–7.90(m, 10H), | CDCl$_3$ | 20<br>100 | 3<br>3 | 4<br>4 | 1<br>2 |

TABLE 2-continued

| Example No. | IR ν value (cm$^{-1}$) | Method | NMR Chemical shift δ value | Solvent | Conc. (ppm) | Evaluation Plants X | Y | Z |
|---|---|---|---|---|---|---|---|---|
| 15 | 1617, 1663 | KBr | 12.92(br, 1H) 2.10(s, 3H), 2,33(s, 3H), 2.87(t, 2H), 2.88(s, 3H), 4.16(t, 2H), 6.70–7.90(m, 10H), 12.82(br, 1H) | CDCl$_3$ | 20 100 | 1 1 | 1 2 | 1 1 |
| 16 | 1613, 1655 | KBr | 0.50–2.00(m, 7H), 1.08(t, 3H), 1.17(t, 6H), 2.41(s, 3H), 2.65(q, 6H), 2.83(s, 3H), 3.93(t, 2H), 7.02(s, 3H), 11.80(br, 1H) | CDCl$_3$ | 20 100 | 4 5 | 4 5 | 5 5 |
| 17 | 1610, 1657 | Neat | 1.10(t, 3H), 1.18(t, 6H), 2.41(s, 3H), 2.41–3.20(m, 8H), 2.87(s, 3H), 4,21(t, 2H), 6.90–7.40(m, 8H), 11.73(br, 1H) | CDCl$_3$ | 20 100 | 2 4 | 4 4 | 4 4 |
| 18 | 1607, 1643, 1663 | KBr | | | 20 100 | 1 2 | 4 4 | 5 5 |
| 19 | 1607, 1660 | KBr | 2.13(s, 3H), 2.28(s, 6H), 2.43(s, 3H), 2.87(s, 3H), 2.99(t, 2H), 4.27(t, 2H), 6.80–7.80(m, 8H), 12.13(br, 1H) | CDCl$_3$-DMSO-d$_6$ | 20 100 | 3 3 | 4 4 | 4 5 |
| 20 | 1615, 1657 | KBr | 0.60–2.00(m, 7H), 2.13(s, 3H), 2.31(s, 3H), 2.40(s, 3H), 2.84(s, 3H), 3.94(t, 2H), 6.80–7.30(m, 3H), 12.16(br, 1H) | CDCl$_3$ | 20 100 | 1 4 | 2 4 | 4 4 |
| 21 | 1613, 1663 | KBr | 2.15(s, 3H), 2.32(s, 3H), 2.40(s, 3H), 2.89(s, 3H), 2.95(t, 2H), 4.20(t, 2H), 6.85–7.35(m, 8H), 12.02(br, 1H) | CDCl$_3$ | 20 100 | 4 4 | 4 5 | 4 4 |
| 22 | 1620, 1665 | KBr | 0.70–2.00(m, 7H), 2.14(s, 3H), 2.40(s, 3H), 2.45(s, 3H), 2.87(s, 3H), 2.96(t, 2H), 6.90–8.00(m, 3H), 12.79(br, 1H) | CDCl$_3$ | 20 100 | 2 2 | 4 4 | 4 5 |
| 23 | 1613, 1667 | KBr | 2.12(s, 3H), 2.35(s, 3H), 2.43(s, 3H), 2.88(s, 3H), 2.90(t, 2H), 4.17(t, 2H), 6.80–8.15(m, 8H), 12.73(br, 1H) | CDCl$_3$ | 20 100 | 3 3 | 4 5 | 2 3 |
| 24 | 1615, 1665 | KBr | 1.27(t, 3H), 2.15(s, 3H), 2.40(s, 3H), 2.79(q, 2H), 2.94(s, 3H), 2.96(t, 2H), 4.23(t, 2H), 6.90–8.15(m, 9H), 12.48(br, 1H) | CDCl$_3$ | 20 100 | 5 5 | 5 5 | 5 5 |
| 25 | 1610, 1660 | Neat | 0.60–2.00(m, 7H), 1.17(t, 6H), 2.32(s, 3H), 2.66(q, 4H), 2.86(s, 3H), 3.93(t, 2H), 4.06(s, 2H), 6.90–7.25(m, 8H), 11.77(br, 1H) | CDCl$_3$ | 20 100 | 1 1 | 1 2 | 4 4 |
| 26 | 1607, 1657 | Neat | 1.18(t, 6H), 2.30(s, 3H), 2.67(q, 4H), 2.89(s, 3H), 2.94(t, 2H), 4.05(s, 2H), 4.15(t, 2H), 6.80–7.40(m, 13H), 11.70(br, 1H) | CDCl$_3$ | 20 100 | 1 1 | 3 3 | 3 3 |
| 27 | 1645 | KBr | 1.24(t, 6H), 1.93(s, 3H), 2.02(s, 3H), 2.58(s, 3H), 2.59(q, 4H), 7.03(s, 3H), 11.37(br, 1H), 12.94(br, 1H) | CDCl$_3$ | 20 100 | 1 2 | 1 1 | 3 4 |
| 28 | 1615, 1653 | KBr | 0.70–2.00(m, 7H), 1.17(t, 6H), 2.17(s, 3H), 2.44(s, 3H), 2.64(q, 4H), 2.88(s, 3H), 4.00(t, 2H), 7.22(s, 2H), 11.90(br, 1H) | CDCl$_3$ | 20 100 | 5 5 | 5 5 | 5 5 |

X: *Oryza sativa* L.
Y: *Echinochloa crusgalli* L.
Z: *Raphanus sativus* L.

What we claim is:
1. A compound of the formula:

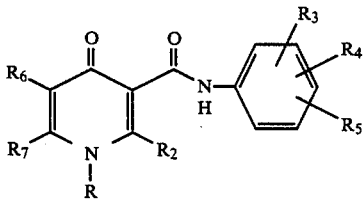

wherein:

R is hydrogen;

R$_2$ and R$_7$ are the same and are each C$_{1-11}$ alkyl; lower alkenyl; lower alkynyl; C$_{3-6}$ cycloalkyl; lower alkoxyalkyl; phenyl-C$_1$-C$_4$-alkyl; or phenyl-C$_1$-C$_4$-alkyl substituted by halogen, lower alkyl, lower alkoxy, or haloalkyl;

R$_3$, R$_4$ and R$_5$ are the same or different and are each hydrogen, halogen, amino, lower alkyl, lower haloalkyl, hydroxy, lower alkoxy, phenyloxy, carboxy, or lower alkoxycarbonyl;

R$_6$ is lower alkyl, phenyl, or phenyl-C$_1$-C$_4$-alkyl; and, when R$_2$ and R$_7$ are both methyl, R$_6$ is lower alkyl, phenyl or phenyl-C$_1$-C$_4$-alkyl; and an addition salt of said compound with an acid or a base.

2. A compound of claim 1, wherein the following moiety

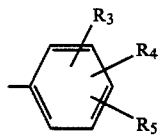

is phenyl; 2-methylphenyl; 2-chlorophenyl; 2,3-dimethylphenyl; 2,6-dimethylphenyl; 2,6-diethylphenyl; 2,6-diethyl-4-substituted phenyl substituted by halo, cyano, nitro, amino, lower alkyl, lower haloalkyl, hydroxy, lower alkoxy, aryloxy, carboxy or lower alkoxy carbonyl; or 2ethyl-6-methylphenyl.

3. A compound of claim 1, wherein the following moiety

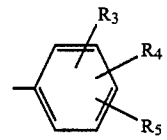

is 2-chloro-6-methylphenyl, 3-chloro-2-methylphenyl, 2-ethylphenyl, 2,3-dichlorophenyl, 2,4-dichlorophenyl, 2,5-dichlorophenyl or 2,6-dichlorophenyl.

4. A compound of claim 1, wherein the R$_2$ and R$_7$ alkyl, lower alkenyl or lower alkynyl group has from 1 to 5 carbon atoms.

5. A compound of claim 1 wherein R$_6$ and R$_7$ are methyl or ethyl.

6. A compound of claim 1, wherein R$_6$ is hydrogen, bromine, methyl or ethyl.

7. A compound of claim 1, wherein —(CH$_2$)$_n$—R$_1$ is methyl, ethyl, propyl, butyl, isobutyl, pentyl, isopentyl or hexyl.

8. A plant growth inhibitor, which comprises an effective amount of the active compound of claim 1 in an inert carrier or solvent.

9. A plant growth inhibitor, which comprises an effective amount of the active compound of claim 2 in an inert carrier or solvent.

10. A compound of claim 1, wherein:

R is hydrogen;

R$_2$ and R$_7$ are the same and are each C$_{1-11}$ alkyl;

R$_3$, R$_4$ and R$_5$ are the same or different and are each hydrogen, halogen, or lower alkyl; and R$_6$ is hydrogen, halogen, lower alkyl, phenyl, or phenyl-C$_1$-C$_4$-alkyl.

11. A plant growth inhibitor, which comprises an effective amount of the active compound of claim 10 in an inert carrier or solvent.

* * * * *

UNITED STATES PATENT AND TRADEMARK OFFICE
CERTIFICATE OF CORRECTION

PATENT NO. : 4,946,497

DATED : August 7, 1990

INVENTOR(S) : YUKIHISA GOTO et al.

It is certified that error appears in the above-identified patent and that said Letters Patent is hereby corrected as shown below:

Column 1, line 13: After "inhibitory" delete the colon (:).

Column 1, line 68: After "formula" insert --(I)--.

Column 5, line 45: After "carboxamide" change period (.) to comma (,).

Column 5, line 50: Change "4oxo" to --4-oxo--.

Column 5, line 55: Change "4oxo" to --4-oxo--.

Column 5, line 56: Change "3pyridine" to --3-pyridine--.

Column 5, line 63: Change "4oxo" to --4-oxo--.

Column 5, line 65: Change "2phenyl" to --2-phenyl--.
Change "3pyridinecarboxamide" to --3-pyridinecarboxamide--.

Column 5, line 68: Change "3pyridinecarboxamide" to --3-pyridinecarboxamide--.

Column 6, line 14: Change "1(4pyridylmethyl)" to --1-(4-pyridylmethyl)--.

Column 6, line 17: Change "4oxo" to --4-oxo--.

Column 6, line 41: Change "ethyl)3" to --ethyl)-3--.

Column 6, line 53: Change "4oxo" to --4-oxo--.

UNITED STATES PATENT AND TRADEMARK OFFICE
CERTIFICATE OF CORRECTION

PATENT NO. : 4,946,497

DATED : August 7, 1990

INVENTOR(S) : YUKIHISA GOTO et al.

It is certified that error appears in the above-identified patent and that said Letters Patent is hereby corrected as shown below:

Column 9, Table 2: Example No. 6, under column "ν value ($cm^{-1}$)", "1627" should read --1627,--.

Column 9, Table 2: Example No. 13, under column "chemical shift $\delta$ value", "2.39 (s, 3H), 2.65 (q,4H)" should be followed by a comma (,).
Example No. 14, under same column, "2.78(s, 3H), 5.16(s, 2H)" should be followed by a comma (,).

Column 11, Table 2: Example No. 15, under column "Chemical Shift $\delta$ value", change "2,33(s, 3H)," to --2.33(s, 3H),--.

Column 6, line 55: Change "1(2phenylethyl)" to --1-(2-phenylethyl--.

Column 6, line 68: Change "3pyridinecarboxamide" to --3-pyridinecarboxamide--.

Column 8, Table 1: Example No. 8 should have a quotation mark (") under the column "Method".

Column 8, Table 1: Example No. 17 should have a quotation mark (") under the column "Method".

Column 11, Table 2: Example No. 19, line 3, under column "Chemical Shift $\delta$ value", change "4,27(t,2H)," to --4.27(t,2H),--.

UNITED STATES PATENT AND TRADEMARK OFFICE
CERTIFICATE OF CORRECTION

PATENT NO. : 4,946,497

DATED : August 7, 1990

INVENTOR(S) : YUKIHISA GOTO et al.

Page 3 of 3

It is certified that error appears in the above-identified patent and that said Letters Patent is hereby corrected as shown below:

Column 11, Table 2, Footnote Y: Change "crusgalli" to --crus-galli--.

Column 14, line 2: Change "2ethyl-6-methylphenyl" to --2-ethyl-6-methylphenyl--.

Column 14, line 15: Change "$R_2$ and $R_7$" to --$R_2$ or $R_7$--.

Column 14, line 18: Change "$R_6$" to --$R_2$-- and insert a comma (",") between "1" and "wherein".

Column 14, lines 20-21: Between "is" and "methyl", delete "hydrogen, bromine".

Signed and Sealed this

Twenty-fifth Day of August, 1992

Attest:

DOUGLAS B. COMER

Attesting Officer

Acting Commissioner of Patents and Trademarks